United States Patent [19]

Brois et al.

[11] Patent Number: 5,274,051
[45] Date of Patent: Dec. 28, 1993

[54] CARBONYL CONTAINING COMPOUNDS VIA RADICAL GRAFTING

[75] Inventors: Stanley J. Brois, Westfield; Jacqueline Ogletree, Whitehouse Station, both of N.J.

[73] Assignee: Exxon Research & Engineering Company, Florham Park, N.J.

[21] Appl. No.: 972,271

[22] Filed: Nov. 5, 1992

[51] Int. Cl.$^5$ .............................. C08F 8/12; C08F 8/30; C07C 69/66; C07C 59/76
[52] U.S. Cl. .................................... 525/383; 525/374; 525/386; 528/222; 560/170; 560/174; 560/190; 562/567; 562/578; 562/590; 564/160
[58] Field of Search ............ 525/383, 386, 374, 333.6, 525/213; 526/316; 528/222; 560/170, 174, 190; 562/567, 578, 590; 564/160

[56] References Cited

U.S. PATENT DOCUMENTS

| | | | |
|---|---|---|---|
| 4,219,437 | 8/1980 | Papanu | 528/222 |
| 4,424,317 | 1/1984 | Serres et al. | 526/316 |
| 4,566,984 | 1/1986 | Bush | 562/583 |
| 4,897,200 | 1/1990 | Smakman | 525/383 |

Primary Examiner—Paul R. Michl
Assistant Examiner—Tae H. Yoon
Attorney, Agent, or Firm—Joseph J. Dvorak

[57] ABSTRACT

Novel carbonyl containing compositions are prepared by contacting, in the presence of a free radical initiator, a first compound selected from the group consisting of saturated hydrocarbons, substituted saturated hydrocarbons, polymers and mixtures thereof with a carbonyl containing compound or mixtures thereof having the structure:

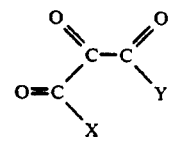

where X and Y are independently selected from OH, OR$_1$, NR$_1$R$_2$ and R$_1$ wherein R$_1$ and R$_2$ are selected independently from the group consisting of aryl radicals or alkyl radicals of from 1 to 18 carbon atoms.

9 Claims, No Drawings

CARBONYL CONTAINING COMPOUNDS VIA RADICAL GRAFTING

FIELD OF THE INVENTION

The present invention relates to novel carbonyl containing compounds of saturated hydrocarbons, especially polymeric hydrocarbons.

BACKGROUND OF THE INVENTION

In U.S. Pat. No. 5,057,564, novel cyclic carbonyl containing compounds are disclosed. These compounds are produced by heating a mixture of a carbonyl compound having an ene reactive carbonyl group with an unsaturated polymer. Although the process and products are quite useful, it nonetheless would be desirable to be able to form carbonyl modified compounds of saturated hydrocarbons, especially saturated polymers.

SUMMARY OF THE INVENTION

Accordingly, novel carbonyl containing compositions are prepared by contacting, in the presence of a free radical initiator, a compound selected from the group consisting of saturated hydrocarbons, substituted saturated hydrocarbons, polymers and mixtures thereof with a carbonyl containing compound or mixtures thereof having the structure:

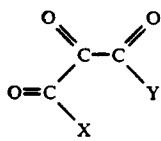

where X and Y are independently selected from OH, $OR_1$, $NR_1R_2$ and $R_1$ wherein $R_1$ and $R_2$ are selected independently from the group consisting of aryl radicals or alkyl radicals of from 1 to 18 carbon atoms.

In general, the contacting is conducted at a temperature and for a time sufficient to produce the novel compositions. Preferably the contacting is conducted at about the decomposition temperature of the radical initiator.

The compositions prepared according to the method of the invention are particularly useful as solution viscosification agents.

GENERAL DESCRIPTION

According to the present invention, novel carbonyl containing compounds are formed by contacting, in the presence of a free radical initiator, a saturated hydrocarbon, a substituted saturation hydrocarbon, a polymer, or mixtures thereof with a carbonyl containing compound or mixtures thereof having the structure:

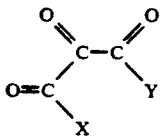

where X and Y are independently selected from OH, $OR_1$, $NR_1R_2$, and $R_1$ wherein $R_1$, and $R_2$ are aryl radicals or alkyl radicals of from 1 to 18 carbon atoms.

The radical-initiated reaction of carbonyl monomers can be applied to a wide spectrum of hydrocarbons which can be selected from the group consisting of normal alkanes such as decane, hexadecane, octadecane, tricosane, paraffins having 10 to about 50 carbons; branched alkanes such as dimethyl hexane, trimethyldecane, tetramethylpentadecane [pristane]; white oils, Nujols, hydrogenated oligomers and co-oligomers of ethylene, propylene, butylene and higher molecular weight olefin oligomers having 10 to about 50 carbons; substituted hydrocarbons consisting of normal and branched alkanes having one or more functional groups such as OH, $O[CH_2CH_2O]_xH, [x=1-10]$, Cl, CN, COOH, COOalkyl, $C[=O]$alkyl, [alkyl contains 1-18 carbons], aryl, and ethylene groups. Typical examples of useful substituted hydrocarbons consist of decanol, octadecanol, ethoxylated octadecanol, stearic acid, ethyl stearate, methyl decyl ketone, tetrapropylbenzene, octadecene, tetrapropylene, tetraisobutylene, mineral oils, and synthetic lubricant oils.

Useful polymers include but are not limited to polymers derived from one or more of the following monomers: ethylene, propylene, butenes, higher alpha-olefins, styrene, allyl esters, vinyl esters, and halides such as vinyl acetetate and vinyl chloride; acrylic acid, acrylonitrile, and the like. Polymers can be linear or branched, and high or low molecular weight [Mn=500 to 10 million]. Homopolymers of ethylene such as high and low density polyethylene, atactic or crystalline polypropylene, polybutene, polyisobutylene homopolymers and copolymers of higher alpha-olefins, copolymers of ethylene with propylene, EPR, which may also contain unconjugated dienes [EPDM], copolymers of ethylene with butenes of higher alphaolefins, copolymers of propylene with butenes, and higher alphaolefins. When dienes such as butadine or isoprene are used in copolymer formation, the resulting polymers are preferably hydrogenated to saturate substantially all of the ethylenic unsaturation. Useful polymers include hydrogenated styrene butadiene block, and tapered copolymers and hydrogenated styrene butadiene block. Since ethylenic unsaturation in polymers sometimes induces undesirable crosslinking during radical grafting, excess olefinic groups should be removed by catalytic hydrogenation.

Typical carbonyl compounds include ketomalonic acid, and esters of ketomalonic acid including alkyl and aryl esters. Other useful keto acids include alpha-ketosuccinic acid, diketosuccinic acid, and any alpha ketohydrocarboic acid, and alpha, beta-diketohydrocarboic acid and their ester and amide derivatives. Useful ketone monomers include dimethyl, diphenyl, and di-tolyl tri-ketones and tetra-ketones.

Useful free radical initiators used in forming the compounds of this invention include dialkyl peroxides such as di-tertiary-butyl peroxide,2,5-dimethyl-2,5-di-tertiary-butyl-peroxyhexane, di-cumyl peroxide; alkyl peroxides such as tertiary-butyl hydroperoxide, tertiary-octyl hydroperoxide, cumene hydroperoxide; aroyl peroxides such as benzoyl peroxide; peroxy esters such as tertiary-butyl peroxypivalate, tertiary-butyl perbenzoate; and azo compounds such as azo-bis-isobutyronitrile. Any free radical initiator with a suitable half life at the reaction temperatures cited above can be used.

When radical grafting in solution, the polymer is dissolved in a suitable solvent such as chlorobenzene, dichlorobenzene, or mineral oil, and heated to temperatures ranging from about 90° C. to about 200° C. depending upon the nature of the free radical initiator being used. The initiator can be added in one dose or dropwise over a suitable time span, usually from 5 to 60 minutes. Another option is to add a mixture of the monomer and peroxide in a suitable solvent to the hydrocarbon, or polymer solution at an addition rate and temperature consistent with the half-life of the radical initiator. The reaction mixture is heated with stirring until infrared and/or nmr analysis indicates that radical addition of the carbonyl monomer to the hydrocarbon or polymer is complete. Depending upon temperature and concentration, reaction times of about 0.1 to about 12 hours are usually sufficient to achieve high levels or monomer utilization. When necessary, radical adducts can be isolated by solvent removal using evaporative techniques, or in the case of polymers, by adding the reaction mixture to a poler solvent such as methanol, or acetone which tend to precipitate the radically functionalized polymer.

Radical grafting of polymers may also be conducted without a solvent, as in a melt, or in polymer processing equipment such as a rubber mill, an extruder, a Banbury mixer, Brabender mixer, and the like. When radical grafting is conducted in bulk, reaction temperatures ranging from about 90° C. to 220° C., and reaction times ranging from about 0.05 to about 1 hour are typical.

In general, the amount of carbonyl compound employed is dictated by the level of functionality desired in the resultant product. Levels of radical grafting onto hydrocarbons and polymers ranging from 0.1 wt. % to about 20 wt. % carbonyl monomer can readily be achieved. If desired, higher levels of functionality can be realized by using additional monomer and free radical initiator.

A typical reaction is illustrated by the following equation:

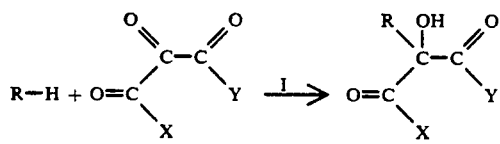

wherein X and Y have the values previously described, RH represents a suitable saturated hydrocarbon, and I represents the free radical initiator.

The amount of free radical initiator used is generally between 1 and 100 wt. % based on the weight of the carbonyl compound, and often depends upon the nature of the free radical initiator, and hydrocarbon or polymer substrate being grafted. The susceptibility of certain polymers to undergo crosslinking and/or chain scission requires careful discretion regarding reagent concentrations, time, temperature, and process conditions since these parameters are all dependent variables in the grafting process. Ordinarily, grafting processes which use from about 10 wt. % to about 50 wt. % levels of free radical initiator, at grafting temperatures ranging from about 90° C. to about 180° C., in an oxygen-free reactor can produce functional polymers with significant levels of appended carbonyl monomers.

EXAMPLES

Example 1

A tenth mole (26.8 grams) of 2,6,10,14-tetramethylpentadecane (pristane), and 0.01 mole (1.74 grams) of diethyl ketomalonate were combined and stirred in a nitrogen blanketed reactor equipped with reflux condensor, thermometer, and an addition funnel. The stirred mixture was heated to about 150° C. and treated with several drops of t-butyl peroxide, a radical initiator. The reaction temperature spontaneously rose from 155° to 160° C. in a few minutes. The peroxide was again added dropwise at a rate of about1 drop per minute. When the peroxide addition was complete (1 ml added), the reaction temperature was increased to 175° C., and kept at 175° C. for two hours. Vacuum distillation of the reaction mixture gave a residue which featured an infrared spectrum with an intense ester carbonyl absorption band at 5.85 microns, and a gc-mass spectrum consisting of several isomers with a molecular ion (m/e=432), which is indicative of a carbonyl modified pristane.

Example 2

Ten grams of methyl nonanoate and 1 gram of diethyl ketomalonate were combined in a nitrogen-blanketed reactor, and heated to about 170° C. One ml of t-butyl peroxide was added in one dose, and the reaction mixture was stirred at 180° C. for about 2.5 hours. Another ml of t-butyl peroxide was then added in one dose, and the stirred mixture was heated at 170° C. for about 7 hours. Evaporation of the mixture gave a residue which featured an infrared spectrum with a characteristic ester carbonyl absorption band at about 8.5 microns, and a gc-mass spectrum with peaks ascribable to isomeric radical adducts of diethyl ketomalonate and methyl nonanoate.

Example 3

Ten grams of polyisobutylene (Mn=950) and 1.5 ml of diethyl ketomalonate were combined in a nitrogen blanketed reactor and heated to 160° C. One ml of t-butyl peroxide was added in one dose to the stirred solution which was heated at 160° C. for about 8 hours. Rotoevaporation gave a residue featuring an infrared spectrum with a strong ester carbonyl absorption band at about 5.8 microns. Elemental analysis indicated that the functionalized polymer contained 1.92% oxygen.

Example 4

Ten grams of ethylene-propylene copolymer (containing 55 wt. % propylene, and having an Mn=54,000), one gram of diethyl ketomalonate and 90 grams of 1,2-dichlorobenzene were combined in a nitrogen blanketed reactor and heated to about 150° C. One ml of radical initiator, t-butyl peroxide, was added dropwise over a half hour period, and the solution was stirred at 160° C. for about 8 hours. Another ml of t-butyl peroxide was added and the reaction mixture was stirred at 160° C. for about 12 hours. The solution was added to a liter of acetone to precipitate the functionalized polymer, which was then dissolved in cyclohexane, and again precipitated in a large volume of acetone. The dried polymer featured an infrared spectrum with a prominent ester carbonyl absorption band at 5.85 microns, and analyzed for 3.76% oxygen.

What is claimed is:

1. A carbonyl containing composition formed by contacting, in the presence of a free radical initiator, a first compound selected from the group consisting of saturated hydrocarbons, substituted saturated hydrocarbons, polymers and mixtures thereof with a carbonyl containing compound having the structure:

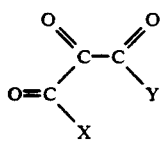

where X and Y are independently selected from OH, OR$_1$, NR$_1$R$_2$ and R$_1$ wherein R$_1$ and R$_2$ are aryl radicals or alkyl radicals of from 1 to 18 carbon atoms.

2. The composition of claim 1 wherein said contacting is at a temperature of from about 90° C. to about 200° C.

3. The composition of claim 2 wherein said first compound is a saturated hydrocarbon having from about 10 to about 50 carbon atoms.

4. The composition of claim 2 wherein said first compound is a polymer having a Mn of from about 500 to about 10 million.

5. The composition of claim 2 wherein the first compound is a substituted hydrocarbon.

6. A composition of matter comprising:
 a) a hydrocarbon radical selected from the group consisting of saturated hydrocarbon, substituted saturated hydrocarbon, and polymer radicals and mixtures thereof, and,
 b) a carboxyl radical having the formula

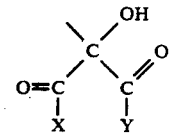

wherein x and are independently selected from OH, OR$_1$, NR$_1$R$_2$ and R$_1$ wherein R$_1$ and R$_2$ are aryl radicals or alkyl radicals of from 1 to 18 carbon atoms.

7. The composition of claim 6 wherein the hydrocarbon radical is a saturated hydrocarbon radical having from about 10 to about 50 carbon atoms.

8. The composition of claim 6 wherein the hydrocarbon radical is a polymeric radical having an Mn of from about 500 to about 10 million.

9. The composition of claim 6 wherein the hydrocarbon radical is a substituted hydrocarbon radical.

* * * * *